United States Patent [19]

Hittman

[11] 4,141,348
[45] Feb. 27, 1979

[54] PRESSURE SENSOR APPARATUS FOR NON-INVASIVELY COMMUNICATING PRESSURE INSIDE A BODY TO THE EXTERIOR THEREOF

[75] Inventor: Fred Hittman, Baltimore, Md.

[73] Assignee: Hittman Corporation, Columbia, Md.

[21] Appl. No.: 726,797

[22] Filed: Sep. 27, 1976

[51] Int. Cl.² ............................................. A61B 5/00
[52] U.S. Cl. ................................ 128/2 A; 128/2.05 D; 128/2.05 E; 73/729; 250/336
[58] Field of Search .................... 128/2 A, 2.1 R, 2 P, 128/2.05 E, 350 V, 2.05 D; 73/398 R, 410, 729; 250/336

[56] References Cited

U.S. PATENT DOCUMENTS

| Re. 26,335 | 9/1960 | Chope | 73/398 |
|---|---|---|---|
| 3,187,181 | 6/1965 | Keller | 250/83 |
| 3,583,387 | 6/1971 | Garner et al. | 120/1 R |
| 3,638,496 | 2/1972 | King | 73/398 R |
| 3,757,770 | 9/1973 | Brayshaw et al. | 128/2 R |
| 3,890,967 | 6/1975 | Elam et al. | 128/145.5 |
| 3,908,461 | 9/1975 | Turpen | 73/398 AR |
| 3,958,558 | 5/1976 | Dunphy et al. | 128/2 P |
| 3,977,391 | 8/1976 | Fleischmann | 128/2 A |
| 4,006,735 | 2/1977 | Hittman et al. | 128/2 A |
| 4,014,319 | 3/1977 | Favre | 128/2 R |
| 4,022,190 | 5/1977 | Meyer | 128/2 A |
| 4,026,276 | 5/1977 | Chubbuck | 128/2.1 R |
| 4,027,661 | 6/1977 | Lyon et al. | 128/2 A |

OTHER PUBLICATIONS

"A Nuclear Intra-Cranial Pressure Sensor", by Bustard et al., IEEE Trans. on Nucl. Science, vol. 4, #1, Feb. 1974, pp. 697–701.

Primary Examiner—Robert W. Michell
Assistant Examiner—Francis J. Jaworski
Attorney, Agent, or Firm—Fleit & Jacobson

[57] ABSTRACT

A pressure sensor for indicating pressure in the animal or human body, such as intracranial pressure, including a housing, a bellows contained within the housing, a body pressure sensing tambour for placing the bellows in communication with pressure in the body so that the pressure will cause the bellows to move as a function of the pressure, output means, such as a radioactive source and associated shielding, contained within the housing and associated with the bellows for providing an output which is a function of the movement of the bellows, and a receiver, such as a radiation detector, located external to the body to receive the output and provide data indicative of the pressure in the body. The pressure sensor includes means associated with the bellows to enable in vivo calibration of the pressure sensor after implantation by establishing a preselected output condition during calibration. An ambient pressure sensing tambour is associated with the bellows for compensating for ambient pressure variations. The bellows is resilient, made of a material and shape which has 100% memory of elastic deformation and has a wall thickness of less than 0.001 inch, in order to provide an output which accurately reflects the pressure being monitored. The bellows has a spring rate which is substantially greater than the spring rate of the pressure sensing and ambient pressure compensating tambours thereby making the pressure sensor essentially insensitive to temperature variations.

19 Claims, 7 Drawing Figures

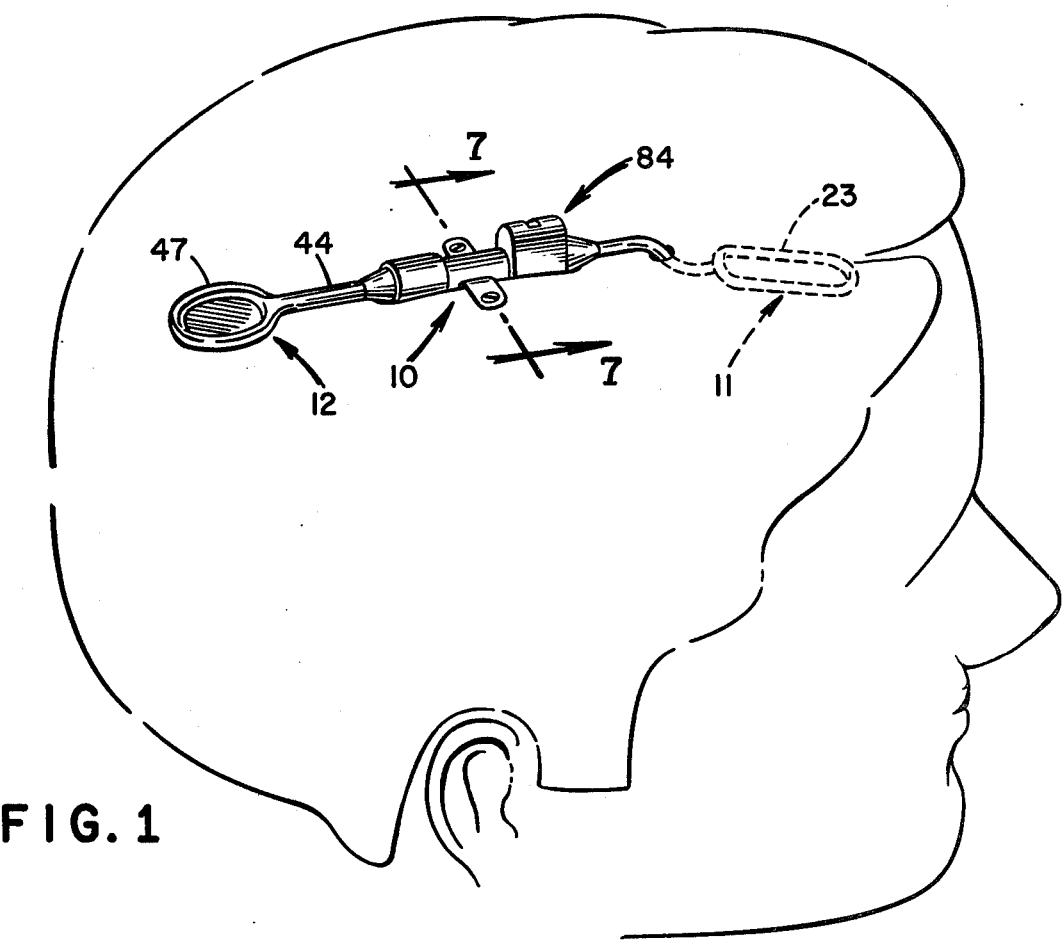
FIG. 1
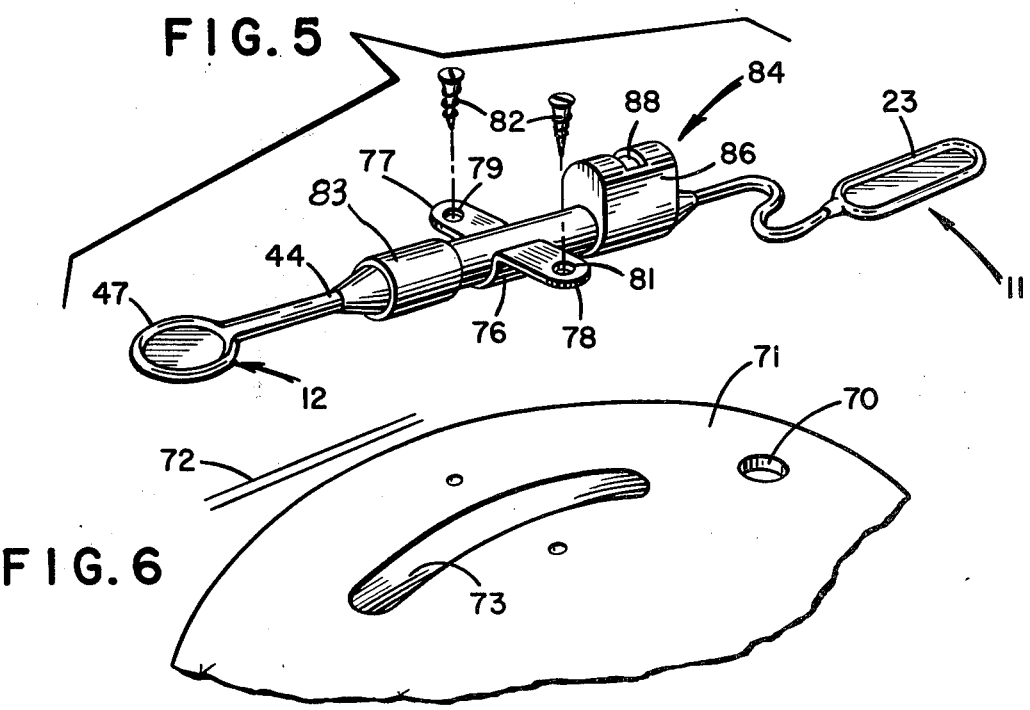
FIG. 5
FIG. 6

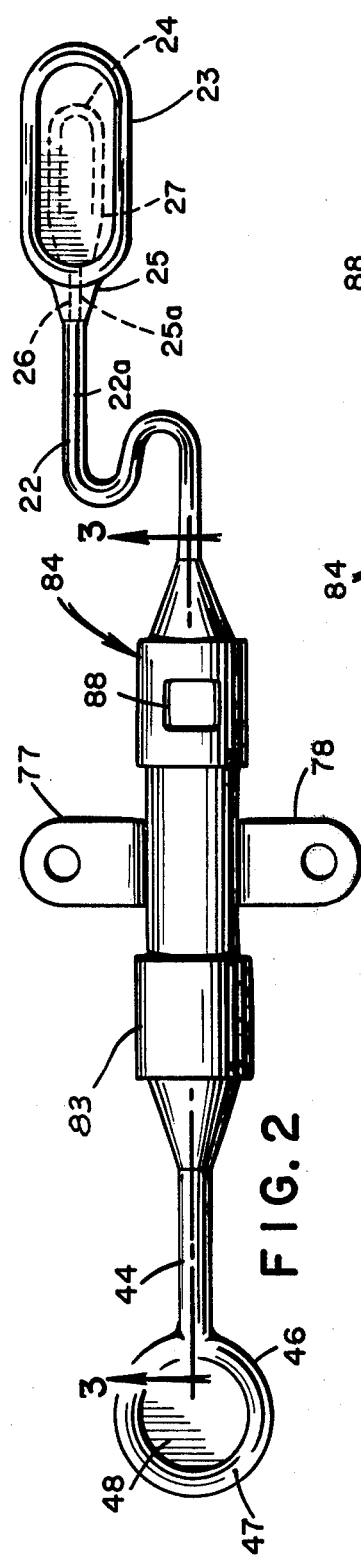
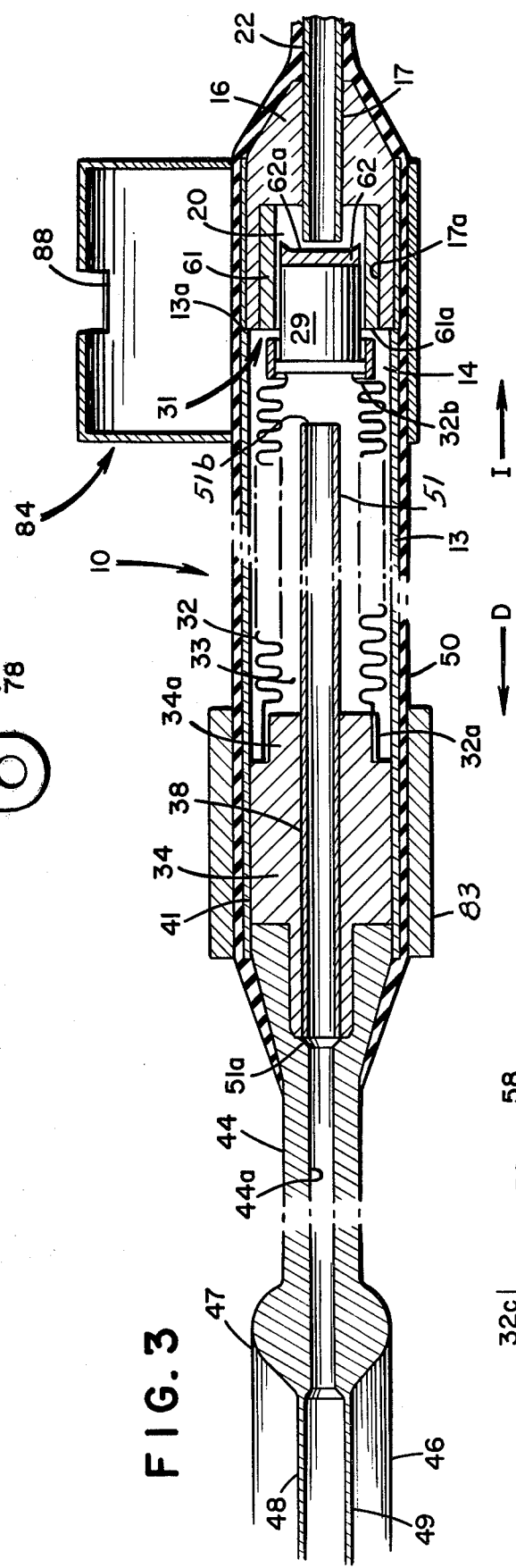
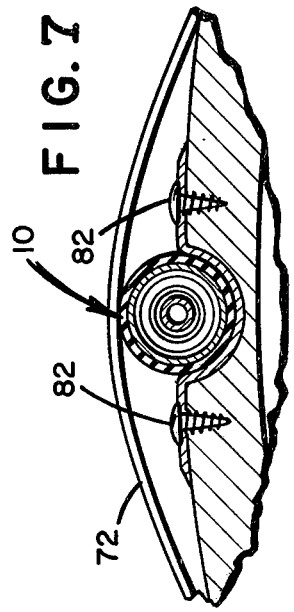
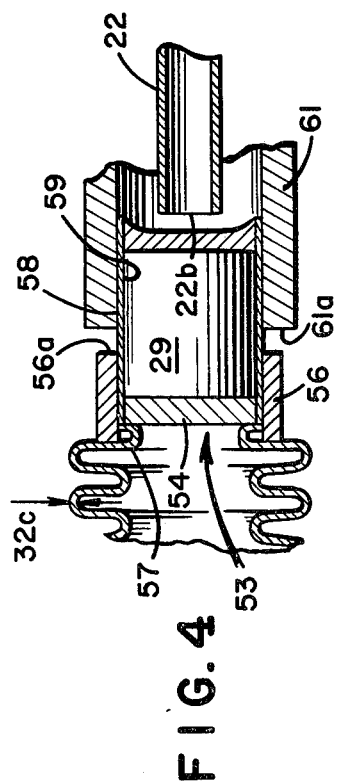
FIG. 2
FIG. 3
FIG. 7
FIG. 4

PRESSURE SENSOR APPARATUS FOR NON-INVASIVELY COMMUNICATING PRESSURE INSIDE A BODY TO THE EXTERIOR THEREOF

CROSS-REFERENCE TO RELATED APPLICATIONS

This invention is related to commonly assigned applications Ser. No. 488,988, filed July 16, 1974, for PRESSURE SENSOR, by Warren C. Lyon et al, and Ser. No. 592,718, filed July 3, 1975, for NON-INVASIVE NUCLEAR DEVICE FOR COMMUNICATING PRESSURE INSIDE A BODY TO THE EXTERIOR THEREOF, by Lewis Fleischmann et al.

BACKGROUND OF THE INVENTION

The need for a non-invasive technique for measuring the pressure in body cavities of animals or humans is recognized as highly desirable for continuous or intermittent monitoring of body conditions. Such cavities as the cranium, vena cava, bladder, and others provide valuable and sometimes critical information for maintaining the well being or survival of an animal or human. For example, it is known that intracranial pressure provides a valuable indication of well being for a variety of clinical conditions, including shock trauma and hydrocephalus.

Accordingly, there is a recognized need for a pressure sensor for continuous or intermittent monitoring of body conditions. In particular, there is a need for a pressure sensor having compensation for ambient pressure variations and low sensitivity to temperature changes. Moreover, there is a need for a sensor which can be calibrated in vivo and which provides an output which accurately reflects the pressure in the animal or human body.

SUMMARY OF THE INVENTION

The pressure sensor of the present invention is fully implantable and contains output means, such as a radioactive source and associated shielding, so that the pressure can be read out non-invasively. In its preferred form, the pressure sensor includes a housing containing a bellows in communication with a body pressure sensing tambour placed in the body and exposed to the pressure to be sensed. An ambient pressure sensing tambour is also associated with the bellows for compensating for ambient pressure variations. The housing is located external to the cavity being sensed and preferably situated just under the skin. The housing also contains the output means, which is associated with the bellows.

The pressure acting upon the body pressure sensing tambour causes the bellows to expand and contract. The movement of the bellows causes the output means to provide an output which is a function of the pressure such as by causing radiation shielding to shield a radioactive source as a function of the pressure sensed. The output is sensed from outside the body by a receiver such as a conventional nuclear counter or crystal detector instrument, in case of a radiation output.

The pressure sensor also includes means associated with the bellows to enable in vivo calibration of the pressure sensor after implantation by reproducing an output condition which is initially established during in vitro calibration. More specifically, and using a radioactive source and associated radiation shielding as illustrative, a stop is provided so that there is a fixed radioactive source to radiation shielding relationship which results in a repeatable radiation output during in vivo calibration.

The bellows is resilient, made of a material and shape which has 100% memory of elastic deformation and has a wall thickness of less than 0.001 inch in order to provide an output which accurately reflects the pressure being monitored. The bellows has a spring constant substantially greater than the spring constant of the body and ambient pressure sensing tambours, which offer effectively no resistance to pressure changes, thereby making the pressure sensor essentially insensitive to temperature variations.

The pressure sensor is fully implantable and does not require any energy source other than the radioactive material, for example, contained in the device. Another major advantage of the sensor is the elimination of leads or other penetrations through the skin to provide power or transmit a signal. With a long-lived radioisotope, such as promethium-145, carbon-14, nickel-63, strontium-90, or americium-241, the inventive pressure sensor can be fully implanted and left in place for long periods of time.

The pressure sensor functions accurately to within several millimeters of water pressure and is unaffected by variations in ambient pressure. Also, it is insensitive to ambient temperature and can be calibrated in vivo. Furthermore, the materials used to construct the sensor are biologically inert and do not pose any health hazard to the animal or human body or make the patient more susceptible to mechanical trauma. The sensor unit is of relatively small size and so does not produce unsightly bulging when implanted subdermally.

Other features and advantages of the invention will be apparent from the following description of the preferred embodiments of the invention as shown in the accompanying drawings.

BRIEF DESCRIPTION OF THE DRAWINGS

FIG. 1 is a perspective view of a preferred embodiment of the implantable non-invasive pressure sensor of the invention in an installed position for monitoring the pressure in an intracranial cavity and communicating the monitored pressure to the exterior of the body;

FIG. 2 is a plan view of the apparatus of FIG. 1;

FIG. 3 is a sectional view taken substantially along line 3—3 of FIG. 3 in the direction of the arrows;

FIG. 4 is an enlarged sectional view of a portion of the apparatus of FIG. 3;

FIG. 5 is an enlarged perspective view of the mounting arrangement for the apparatus of FIG. 1;

FIG. 6 is a perspective view of a portion of the skull of a patient prior to installation of the apparatus of the invention; and FIG. 7 is a sectional view taken substantially along lines 7—7 of FIG. 1 in the direction of the arrows.

DESCRIPTION OF THE PREFERRED EMBODIMENTS

Referring now to the drawings and to FIGS. 1 and 2 in particular, there is shown the pressure sensor apparatus of the invention with a housing designated generally by the numeral 10, and a body pressure sensing means designated generally by the numeral 11 and connected to the housing 10 for sensing the pressure in a body portion such as a cavity. Ambient pressure sensing means, designated generally by the numeral 12, is also connected to the housing 10 and is responsive to ambient pressure to compensate for changes in ambient pressure during the operation of the apparatus. Although the pressure sensor apparatus of the invention is shown in an installed position on the head of a human body for non-invasively monitoring intracranial cavity pressure and communicating it to the exterior, it should be understood that this is only a preferred example of the invention and that it is equally adaptable for monitoring pressure in other areas of the body, both animal and human. Therefore, while the description to follow will be directed to the use of the invention for monitoring intracranial cavity pressure, it should be understood that the invention is equally applicable to monitoring pressure in other body portions and cavities.

Referring now to FIG. 3, and as specifically illustrative of the invention, the housing 10, which is preferably formed of titanium, is of tubular shape having a side wall 13 defining an interior 14. A first support member 16, also preferably formed of titanium, has a central bore 17 positioned within one end of the housing 10 in sealing relationship with the housing side wall 13 by means of an epoxy resin or the like. Preferably, an annular shoulder 13a is formed in the housing side wall 13 for positioning the support member 16 in a precise location within the housing 10 as will be explained hereinafter. The first support member central bore 17 is provided with a portion 17a of substantially enlarged diameter defining a recess 20 which communicates with the interior 14 of the housing 10.

The body pressure sensing means 11 includes a fluid conduit 22 of deformable metallic material, preferably titanium, which has been heat treated for deformability, one end 22a of which is arranged to be connected to the body pressure sensing device or tambour 23 having an interior 24 which is arranged to be positioned within a body cavity such as the intracranial cavity of FIG. 1.

The tambour 23 is formed of a suitable elastomeric material such as medical grade Silastic rubber and is of a substantially flat configuration including a neck portion 25 in the wall of which is molded a helical spring 26, preferably of stainless steel, for imparting rigidity to the neck portion 25. The neck portion 25 includes a central bore 25a which communicates with the interior 24 of the tambour 23 and which is arranged to receive the end 22a of the conduit 22 as shown in FIG. 2. Preferably, a U-shaped clip 27 of tantulum or the like is disposed within the interior 24 of the tambour 23 for maintaining the side walls of the tambour in spaced-apart relationship and to serve as a locating means for the tambour with the use of X-rays. The tambour 23, the fluid conduit 22 and the communicating portions of the housing interior 14, including the recess 20, are filled with a pressure transmitting fluid through which the pressure sensed by the tambour 23 in the body cavity is transmitted to the housing interior 14.

The conduit 22 is inserted through the bore 17 with the end 22b of the conduit 22 extending through the bore 17 into the recess 20 as shown best in FIGS. 3 and 4. Sealing engagement between the conduit 22 and bore 17 is obtained by means of epoxy resin or the like. Thus, the conduit end 22b communicates with the recess 20 and with the housing interior 14.

The output means of the pressure sensor apparatus preferably comprises a source 29 of radioactive material, normally in the form of a shaped article, disposed within the housing interior 14 together with associated radiation shielding means designated generally by the numeral 31. Means are provided in the housing interior 14 for resiliently urging the radioactive material and radiation shielding into a shielding relationship. More specifically, resilient means such as a bellows 32 having an interior 33 is disposed within the housing interior 14, one end 32a of which is mounted on a necked-down portion 34a of a second support member 34, preferably formed of titanium, suitably mounted in the other end of the housing 10 in sealing engagement with the housing side wall 13 by means of an epoxy resin or the like. The other end 32b of the bellows 32 is closed as will be explained hereinafter.

The second support member 34 is provided with a central bore 38 and the necked-down portion 34a is arranged to support the bellows end 32a in a sealing relationship therewith by means of an epoxy resin 41 or the like.

Bellows 32 is made of a resilient material, preferably a metal such as gold-plated nickel. The bellows has a wall thickness 32c which is less than 0.001 inch and preferably less than about 0.0005 inch. The most preferred wall thickness range is between about 0.00025 and 0.00033 inch. The bellows has a length, typically about ½ inch, which varies according to the pressure which the pressure sensor apparatus is intended to monitor. By providing the bellows with a wall thickness of less than 0.001 inch and a corresponding spring rate, the bellows will typically travel (contract or expand) a distance of about 0.050 to 0.060 inch when the body pressure sensing tambour 23 is exposed to pressure variations such as those normally found in monitoring intracranial pressure. In this manner, a relatively large movement (contraction or expansion) of bellows 32 is caused by the pressure being monitored. Since the bellows (spring) is operated or stressed within its elastic range, it will return to its equilibrium position when the stress (pressure) is removed. In other words, the bellows has 100% memory of elastic deformation. Accordingly, the pressure sensor apparatus is capable of more accurately monitoring pressure changes in the animal or human body than conventional pressure sensors.

The second support member 34 receives the end of fluid conduit 44 which is formed of a suitable elastomeric material such as medical grade Silastic rubber and has a central passage 44a. Fluid conduit 44 is connected to an ambient pressure sensor or tambour 46 forming the ambient pressure compensating means 12. The tambour 46 is formed of a flexible material, preferably an elastomeric material such as medical grade Silastic rubber, and includes an annular peripheral portion 47 and a recessed central portion 48 defining an interior 49 which communicates with the fluid conduit central passage 44a. A suitable adhesive such as a medical grade Silastic adhesive, seals the fluid conduit 44 to the second support member 34 and the tambour.

A rigid metal tube 51, preferably formed of titanium, is also sealed in second support member 34, such as by a Silastic adhesive, and extends through the central bore 38 of the second support member 34 into the bellows interior 33 to communicate the interior 49 of the tambour 46 with the bellows 32. The other end 51b of the tube 51 forms a stop for the bellows end 32b.

In order to transmit the sensed ambient pressure to the interior of the bellows 32, the interior of tambour 46, the fluid conduit 44, the bellows interior 33 and the tube 51 are filled with a pressure transmitting fluid, isolated by means of the bellows 32 from the pressure transmitting fluid in the body pressure sensing means 11. In the preferred embodiment, all of the exposed metallic surfaces of the sensing apparatus of the invention are coated with a suitable biocompatible material, such as a medical grade Silastic. As shown in the drawings, this Silastic coating 50 extends from the fluid conduit connection 44 to tambour 46 to the joint between the metal conduit 22 and the neck portion 25 of tambour 23.

In the illustrated embodiment, the radiation shielding means 31 includes a first portion 53 of radiation shielding material such as tantalum having a cup-shaped configuration. The first portion 53 preferably includes an end plate 54, typically in the form of a disc, and an annular side member 56 both mounted on the other end 32b of the bellows 32 in closing relationship therewith as shown best in FIG. 4.

The radiation shielding means first portion 53 is mounted on an inwardly directed channel portion 57 adjacent the last accordion pleat in the bellows 32, and a tubular sleeve portion 58 extends axially outward therefrom which together define an enclosure 59. The end plate 54 is adhesively secured in the end of the enclosure by a suitable adhesive such as an epoxy resin closing the end 32b of the bellows 32. Similarly, side member 56 is adhesively secured by means of an epoxy resin to sleeve portion 58.

The radiation shielding means also includes a second portion 61 in the form of a tubular sleeve of radiation shielding material, also preferably made of tantalum, which is press-fitted or the like within the recess 20 of the first support member 16. It can be seen that the second portion 61 extends throughout the depth of the recess 20 and has a forward end edge portion 61a terminating flush with the end of the first support member 16 abutting the housing side wall shoulder 13a. Thus, the second portion end 61a is precisely positioned axially in the housing interior 14 adjacent the end edge portion 56a of the first portion side member 56.

Radioactive source 29 is mounted on the end 32b of the bellows 32 and is accommodated for guiding movement within the radiation shield means second portion 61 disposed in the recess 20. As will be appreciated, however, the radiation shielding means rather than the radioactive source 29 may be mounted on bellows 32, such an arrangement merely representing an obvious reversal of cooperating parts. The radioactive source 29, which is preferably of cylindrical shape, has an outer diameter conforming generally to the inner diameter of the bellows sleeve portion 58 and is adhesively secured within the enclosure 59 defined by the tubular sleeve portion 58 by means of a suitable adhesive such as an epoxy resin.

The bellows 32 resiliently urges the radioactive source 29, together with the sleeve portion 58, in the direction of the arrow I into the recess 20 with the edge portion 56a of the radiation shielding means first portion side member 56 in adjacent cooperating relationship with the edge portion 61a of the tubular sleeve forming the radiation shield means second portion 61 to establish a shielding relationship with the radioactive source 29. The end cap 62 is therefore disposed adjacent the outlet end 22b of the pressure transmitting fluid conduit 22 as will be discussed in more detail hereinafter.

The outer diameter of the bellows sleeve portion 58 is selected to produce a loose-fitting relationship with the inner surface of the sleeve forming the radiation shielding means second portion 61 so that fluid introduced into the recess 20 from the end 22b of conduit 22 may flow freely therebetween and through a gap between the first and second end edge portions 56a and 61a, respectively, to fill the interior 14 of the housing 10 on the outside of the bellows 32. It should be understood that in the assembled apparatus of the invention before installation in the body there is virtually no pressure differential in the housing 10 between the pressure-transmitting fluids on opposite side of the bellows 32. In this condition, there is a gap as will be discussed in more detail hereinafter between the adjacent end edge portions 56a and 61a of the first and second portions 53 and 61, respectively. When the apparatus is installed in the body, the normal fluid pressure in the body cavity slightly increases the pressure on the tambour 23 introducing additional pressure transmitting fluid into the housing interior 14 on the outside of bellows 32, moving the bellows in the direction of the arrow D, and thereby increasing slightly the gap between the end edge portions 56a and 61a.

In the operation of the invention after installation, an increase in body pressure is sensed in the body cavity by the body pressure sensing device or tambour 23, the sensed pressure is transmitted by the pressure transmitting fluid flowing into the support member recess 20 through the end 22b of conduit 22 around the end cap 62 through the gap between the edge portions 56a, 61a to move the bellows 32 together with the radiation shielding means first portion 53 and the radioactive source 29 in the direction indicated by the arrow D in opposition to the urging force exerted by the bellows. During this movement, the radiation shielding means first and second portions 53, 61 move apart increasing the gap proportionally with the increase in cavity pressure thereby modifying the shielding relationship between the shielding means 31 and radioactive source 29 to expose more of the radioactive source in accordance with the magnitude of the cavity pressure. The radioactive output of the exposed portion of the radioactive source 29 may then be sensed by a receiver means (not shown) such as a conventional nuclear counter or crystal detector disposed externally of the housing 10 and the body.

The provision of the ambient pressure sensing means 12 permits the pressure sensor apparatus of the invention to be responsive to pressure changes in the body cavity regardless of ambient pressure changes. More specifically, ambient pressure changes are imposed equally on both the ambient pressure sensing means 12 and body pressure sensing means 11 whereby the sensing apparatus of the invention responds to body cavity pressure changes only.

The pressure sensor apparatus of the present invention is essentially insensitive to ambient temperature variations as well as temperature variations which may occur inside the animal or human body whose pressure is being monitored. More specifically, bellows 32 has a spring constant which is orders of magnitude greater than the spring constant of pressure sensing tambours 23 and 46 which offer effectively no resistance to pressure changes. Accordingly, any volumetric changes in the pressure transmitting fluid due to temperature variations in the body or ambient temperature changes will act to distend the body pressure sensing tambour 23 and ambient pressure sensing tambour 46, respectively, instead of causing a movement (contraction or expansion) of bellows 32. Therefore, temperature variations whether external or internal to the cavity being monitored do not effect or change the output of the pressure sensor apparatus and therefore do not cause erroneous pressure measurements. Moreover, all of the components of the pressure sensor apparatus are implanted in close proximity to each other and therefore are essentially at a constant temperature (i.e., body temperature). Since none of the components of the pressure sensor are temperature sensitive and since all of the components are essentially at the same temperature, the sensor is temperature insensitive for this additional reason.

A unique feature of the present invention is the provision of means to enable in vitro calibration of the pressure sensor apparatus after implantation by reproducing an output condition which is initially established during in vivo calibration. More specifically, in accordance with the present design, and using a radioactive source and associated radiation shielding as illustrative, a stop is provided so that there is a fixed radioactive source to radiation shielding relationship which results in a repeatable radiation output during calibration. This fixed radioactive source to radiation shielding relationship is set at a point where the bellows is essentially in its equilibrium condition (i.e. where there is essentially a zero pressure differential across the bellows). This stop is provided in the embodiment illustrated by the end 22b of fluid conduit 22. After the pressure sensor apparatus is implanted, the surgeon can calibrate the instrument by pressing on the ambient pressure compensating tambour 46 which will cause the pressure transmitting fluid in the interior of tambour 46, the bellows interior 33 and the tube 51 to move bellows 32 and radioactive source 29 in the direction of arrow I so that the end cap 62 abuts against the end 22b of conduit 22. In this extreme stop position, there is a fixed and repeatable amount of radiation emitted from the pressure sensor apparatus, representing in effect a zero (or known) pressure differential across the bellows.

Because the housing 10 in which the output means of the pressure sensor apparatus is housed is implanted under the scalp, for example, the scalp or other body tissue surrounding the housing will attenuate the radiation output signal as a function of the scalp thickness. Accordingly, in the laboratory before implantation, the radiation output from the pressure sensor apparatus with bellows 32 and radioactive source 29 at the extreme stop position is measured for a range of simulated scalp thickness, for example, 3 millimeter, 6 millimeter, and 9 millimeter of simulated scalp thickness. This measurement is also made over a range of pressures which corresponds to the pressures which would normally be encountered in the particular body cavity being monitored. Then, a family of curves is produced which correlate the radiation output with the pressure being monitored for each scalp thickness. After the sensor is implanted, the surgeon performs the in vivo calibration as described above by pressing on the ambient pressure compensating tambour 46 and forcing bellows 32 and radioactive source 29 to the extreme stop position. The radiation count obtained will fall on or near one of the family of curves. This curve is then used in monitoring the pressure or this data is used to properly establish the relationship of radioactive counts and pressure differential in a direct read out instrument.

To insure a long life for the pressure sensing apparatus of the invention commensurate with body compatability, it has been found that specific non-reactive fluids and elastomeric materials eliminate such reactions. More specifically, the best results that have been obtained are when the elastomeric material of the various components are formed, in one example, from a Silastic type of silicone rubber and the pressure transmitting fluids are either castor oil, mineral oil, or synthetic cerebrospinal fluid between which there is virtually no chemical or physical reaction thereby insuring proper functioning of the pressure sensor apparatus throughout its life. It has also been found that when the pressure transmitting fluid is a silicone oil, the outstanding results of the invention are accomplished when the elastomeric materials are selected from the group consisting of butyl, neoprene, Buna N and Viton A rubbers. It should be understood, however, that other elastomeric materials and fluids perform satisfactorily but with less desirable results.

One major concern in selecting a fluid is the osmotic pressure effects produced after implantation. In order to eliminate these effects, it is preferred that a simulated cerebrospinal fluid be used as the pressure transmitting medium and it may be used with all materials of construction as it will be compatible with body fluids and will not leak through the elastomeric materials as a consequence of osmotic pressure.

In the use of the invention to monitor the fluid pressure within an intracranial cavity and with reference to FIGS. 5-7, the common practice is to provide a burr hole or aperture 70 within the bony structure of skull 71 overlying the intracranial cavity through which the metallic fluid conduit 22 is inserted, the body pressure sensing device 23 being suitably disposed within the intracranial cavity. A body pressure sensing means such as tambour 23 is normally positioned subdurally. However, it should be appreciated that the invention also contemplates positioning the body pressure sensing means 11 epidurally in which case the shape and size of the tambour will be appropriately changed. The housing 10, together with the ambient pressure compensating device 12, are mounted on the outer surface of the skull 71 under the scalp 72.

The apparatus of the invention includes means for permanently mounting the housing 10 and ambient pressure sensing means 12 subcutaneously on the outer surface of the skull 71 in an inconspicuous, securely retained position. More specifically, an elongated concave groove 73 is formed within the outer surface of the skull 71 adjacent the burr hold 70, and mounting means are provided for securing the housing 10 in a seated relationship within the groove 73. The mounting means includes at least one tab 74 on the housing 10 as shown best in FIG. 5. The tab 74 includes an intermediate portion 76 of arcuate cross-sectional shape for accommodating the tubular housing 10 in underlying engagement therewith. The tab portion 76 is secured to the outer surface of the housing 10 by suitable means such as a body compatible adhesive, welding or the like. The tabs 74 also include oppositely disposed end portions 77 and 78 extending laterally outward of the housing 10 secured within the intermediate portion 76.

Openings 79, 81 are provided in the tab end portions 77, 78 respectively for accommodating screw means such as screws 82 extending therethrough in threaded engagement with the underlying bone of the skull 71, and with the end portions 77, 78 in overlying engagement with the outer surface of the skull 71, the tab intermediate portion 76 and housing 10 being accommodated within the groove 73. Also, accommodated within groove 73 is spacer 83 which surrounds the end of housing 10 adjacent pressure sensing tambour 46. The thickness of spacer 83 is the same as the thickness of tab intermediate portion 76 so that housing 10 will lie relatively flat in groove 73. Spacer 83 may be made from any suitable material such as a plastic or a radiation shielding material such as tantalum.

The apparatus of the invention also includes means for collimating the output of the pressure sensor apparatus. The collimator 84 comprises radiation shielding 86 mounted on the housing 10 adjacent the gap between the end edge portions 56a and 61a through which the radiation is emitted. The collimator 84 completely surrounds the housing 10 and has an opening or aperture 88 which extends completely through the radiation shielding on the side of the housing 10 which faces away from the skull 71. The radiation shielding 86 is preferably solid except for the aperture 88 and extends away from the housing 10 in the area in which the aperture 88 is positioned to better collimate the radiation. The length to width ratio of aperture 88 is selected in conventional manner to produce the desired collimation. By this means, the distance between the radioactive source 29 and the radiation detector (not shown) may be varied within reasonable limits without changing the count rate which is detected. Also, the radiation shielding 86 prevents downwardly directed radiation into the body, so that the radioactive output of source 29 is confined in a non-attenuating manner to the upward direction to permit easy detection by an externally positioned detection device.

The strength of the radioactive source 29 need only be of an extremely low order of magnitude, typically less than 10 microcuries, a magnitude far less than that at which the adjacent body tissue may be adversely affected. However, it should be characterized by an extremely precise and uniform output rate which accurately reflects the changes in fluid pressure within the body cavity throughout its range of operation. The preferred radioisotopes used in the present invention are promethium-145, carbon-14, nickel-63, strontium-90 and americium-241, and, to obtain the proper radioactive output from the source 29, it should be in the form of a shaped article of highly homogeneous composition.

The radioactive source 29 typically comprises promethium-145 chloride ($PmCl_3$), for example, uniformly distributed and absorbed onto an inert carrier such as diatomaceous earth and uniformly distributed throughout a suitable binder such as an epoxy resin. Sources 29 of this composition are extremely uniform regarding the concentration or distribution of the radioisotope.

Although the invention has been described in terms of a single preferred embodiment, nevertheless, changes and modifications may be made within the scope of the invention. For example, the pressure sensor apparatus as illustrated provides an output which is a direct function of the pressure being monitored since the output increases with increasing body cavity pressure. However, as will be appreciated by one of ordinary skill in the art, the sensor can also be constructed so that the output is an indirect function of the pressure by mounting the radioactive source and the associated radiation shielding so that the radioactive source is increasingly shielded by the radiation shielding as the pressure being monitored increases. In this type of arrangement, the in vivo calibration is performed in the same manner as described herein except that the output will be a repeatable maximum output rather than a repeatable minimum output. Also, while a radioactive source and associated radiation shielding have been illustrated as the output means it will be appreciated that other output means can be employed without altering the basic characteristics of the invention. For example, the output means could comprise a resonant L-C circuit having a variable capacitor or inductor in which bellows 32 is mechanically connected to the variable component to vary the value of capacitance or inductance and hence the resonant frequency of the L-C circuit in response to the pressure changes in the body cavity being monitored. The output could then be detected by a variable-frequency oscillator, for example, or other means well known in the art. Accordingly, the invention should not be limited by the specific embodiment illustrated but only as defined in the appended claims.

I claim:

1. A pressure sensor apparatus for indicating pressure in the body comprising a housing, a bellows contained within said housing wherein said bellows and said housing define a first chamber and a second chamber within said housing, means for placing said first chamber in communication with said pressure in the body so that said pressure will cause said bellows to move as a function of said pressure, means for placing said second chamber in communication with an ambient pressure comprising an ambient pressure sensing means for sensing ambient pressure and connecting means for connecting said ambient pressure sensing means with said second chamber, output means contained within said housing and associated with said bellows for producing an output which is a function of the movement of said bellows to a receiver means located external to said body to provide data indicative of said pressure and means for calibrating said apparatus in vivo by reproducing an output during in vivo calibration which is established during in vitro calibration comprising a stop means positioned within said first chamber for limiting movement of said bellows to a predetermined position within said housing, said stop means extending through said housing having a first end at a predetermined position within said first chamber, and a second end outside the housing wherein said second end is in communication with said pressure in the body, wherein said bellows is adapted to move to said predetermined position when external pressure is provided to said ambient pressure sensing means.

2. The pressure sensor of claim 1, wherein said stop means comprises a conduit made of a metallic material.

3. The pressure sensor of claim 2 wherein said conduit is titanium.

4. A pressure sensor apparatus for indicating pressure in the body comprising a housing, a bellows contained within said housing wherein said bellows and said housing define a first chamber and a second chamber within said housing, means for placing said first chamber in communication with said pressure in the body so that said pressure will cause said bellows to contrast and expand, means for placing said second chamber in communication with an ambient pressure comprising an ambient pressure sensing means for sensing ambient pressure and connecting means for connecting said ambient pressure sensing means with said second chamber, output means contained within said housing for producing an output which is a function of said pressure, said output means having at least two components, the first of said two components being operatively connected to said bellows and moveable therewith when said bellows expands and contracts, the second of said two components positioned within said first chamber and operatively associated with said first component but not moveable with said bellows so that when said first component moves the output of said output means varies as a function of said pressure, the output of said output means being adapted to being sensed by a sensor means located external to said body and which is responsive to said output to provide data indicative of said pressure and means for calibrating said apparatus in vivo by reproducing an output during in vivo calibration which is established during in vitro calibration comprising a stop means positioned within said first chamber for limiting movement of said bellows to a predetermined position within said housing, said stop means extending through said housing having a first end at a predetermined position within said first chamber, and a second end outside the housing wherein said second end is in communication with said pressure in the body, wherein said bellows is adapted to move to said predetermined position when external pressure is provided to said ambient pressure sensing means.

5. The pressure sensor of claim 4, wherein said stop means comprises a conduit made of a metallic material.

6. The pressure sensor of claim 5 wherein said conduit is titanium.

7. The pressure sensor apparatus of claim 4 wherein said first component comprises a nuclear source extending within said first chamber and said second component comprises a shield means positioned within said first chamber for partially shielding said nuclear source to provide an output when the bellows is at said predetermined position.

8. A pressure sensor apparatus for indicating pressure in the body comprising a housing, a bellows contained within said housing wherein said bellows and said housing define a first chamber and a second chamber within said housing, first flexible means associated with said first chamber and adapted to move as a function of the pressure in said body, a pressure transmitting fluid contained within said first chamber and communicating with said first flexible means so that said pressure acting upon said first flexible means will cause said bellows to contract and expand as a function of said pressure, output means contained within said housing having first and second components cooperating to produce an output, said first component being operatively associated with said bellows and moveable therewith and said second component positioned within said first chamber and being operatively associated with said first component but not moveable with said bellows so that said output produced by said output means is a function of the contraction and expansion of said bellows, ambient pressure sensing means associated with said second chamber for compensating for ambient pressure variations acting upon said flexible means said ambient pressure sensing means comprising second flexible means associated with said second chamber and adapted to move as a function of the ambient pressure and a second pressure transmitting fluid contained within said second chamber and communicating with said second flexible means so that said ambient pressure acting upon said second flexible means will be communicated to said bellows, whereby said output is sensed by a sensor means located external to said body to provide data indicative of said pressure, and means for calibrating said apparatus in vivo by reproducing an output during in vivo calibration which is established during in vitro calibration comprising a stop means positioned within said first chamber for limiting movement of said first component to a predetermined position within said housing with respect to said second component, said stop means extending through said housing having a first end at a predetermined position within said first chamber, and a second end outside the housing wherein said second end is in communication with said pressure in the body, wherein said bellows is adapted to move to said predetermined position when external pressure is provided to said ambient pressure sensing means.

9. The pressure sensor apparatus of claim 8 in which said first and second flexible means each comprises a first and second flexible tambour made of a material which offers effectively no resistance to pressure changes in said body.

10. The pressure sensor apparatus of claim 5 wherein said external pressure to move said bellows means to said predetermined position is provided by pressing on said second flexible tambour.

11. The pressure sensor of claim 8, wherein said stop means comprises a conduit made of a metallic material.

12. The pressure sensor of claim 11 wherein said conduit is titanium.

13. The pressure sensor apparatus of claim 8 wherein said first component comprises a nuclear source extending within said first chamber and said second component comprises a shield means positioned within said first chamber for partially shielding said nuclear source to provide an output when the bellows is at said predetermined position.

14. A pressure sensor apparatus for indicating pressure in the body comprising a housing, a bellows contained within said housing, flexible means associated with said housing and adapted to move as a function of the pressure in said human body, a pressure transmitting fluid contained within said housing and communicating with said flexible means so that said pressure acting upon said flexible means will cause said bellows to contract and expand as a function of said pressure, output means contained within said housing having first and second components cooperating to produce an output, said first component being operatively associated with said bellows and said second component being operatively associated with said first component but not moveable with said bellows so that said output produced by said output means is a function of the contraction and expansion of said bellows, stop means associated with said first component for reproducing an output during in vivo calibration which is established during in vitro calibration, said stop means extending through said housing having a first end at a predetermined position within said housing, and a second end outside the housing wherein said second end is in communication with said flexible means, ambient pressure sensing means associated with said bellows for compensating for ambient pressure variations acting upon said flexible means whereby said output is sensed by a sensor means located external to said body to provide data indicative of said pressure and said apparatus may be calibrated by pressing on said ambient pressure sensing means to cause said first component to move to a stop position defined by said stop means to produce said calibration output.

15. The pressure sensor apparatus of claim 14 in which said flexible means associated with said housing comprises a flexible tambour made of a material and of such shape which offers effectively no resistance to pressure changes in said body.

16. The pressure sensor apparatus of claim 14 in which said ambient pressure compensation means comprises second flexible means associated with said housing and adapted to move as a function of the ambient pressure and a second pressure transmitting fluid contained within said housing and communicating with said second flexible means so that said ambient pressure will be communicated to said bellows.

17. The pressure sensor apparatus of claim 16 which said second flexible means comprises a flexible tambour which offers effectively no resistance in pressure changes.

18. A pressure sensor apparatus for indicating pressure in the animal or human body, particularly intracranial pressure, comprising a housing, a bellows contained within said housing, first flexible means associated with said housing and adapted to move as a function of the pressure in said body, a first pressure transmitting fluid contained within said housing on one side of said bellows and communicating with said first flexible means so that said pressure acting upon said first flexible means will cause said bellows to contract and expand as a function of said pressure in said body, output means contained within said housing and operatively associated with said bellows to produce an output which is a function of the contraction and expansion of said bellows, second flexible means associated with said housing, a second pressure transmitting fluid contained within said housing on the other side of said bellows and communicating with said second flexible means, and means for calibrating said apparatus after implantation whereby said output is sensed by a sensor means located external to said body to provide data indicative of said pressure in said body and said apparatus is capable of being calibrated in vivo by providing a stop means within said housing on said one side of said bellows for limiting movement of said bellows to a predetermined position, said stop means extending through said housing having a first end at a predetermined position within said housing, and a second end outside the housing wherein said second end is in communication with said first flexible means, whereby the apparatus is calibrated by pressing on said second flexible means to move said bellows into contact with said stop means, and wherein the output produced by said output means when the bellows is in contact with said stop means in the body can be compared with the output outside the body.

19. An intracranial pressure sensor apparatus of the type to be positioned between the scalp and skull and having a pressure transferring mechanism extending through the skull comprising a rigid, transfer housing adapted to be positioned between the skull and scalp, bellows means mounted in said housing to divide said housing into first and second chambers, said transfer housing having inlet means connected to said first chamber and outlet means connected to said second chamber, first pressure sensing means connected at one end to said inlet means and having its other end adapted to be positioned inside the skull, a first fluid contained within said first pressure sensing means and said first chamber, said pressure sensing means being flexible and impermeable to said first fluid, whereby pressure acting upon said first pressure sensing means within the skull will cause said bellows means to move as a function of said pressure, means contained within said housing and associated with said bellows means for communicating the movement of said bellows means to a receiver means located external to said scalp to provide data indicative of said pressure acting upon said first pressure sensing means, second pressure sensing means connected to said outlet means and adapted to be exposed to pressure between the scalp and skull, a second fluid contained within said second pressure sensing means and said second chamber, said second pressure sensing means being flexible and impermeable to said second fluid, said second pressure sensing means acting to compensate for changes in ambient pressure externally of the scalp, and means for calibrating said apparatus in vivo by reproducing an output during in vivo calibration which is established during in vitro calibration, said calibration means comprising a stop means for said bellows means, said stop means extending through said housing having a first end at a predetermined position within said housing, and a second end outside the housing wherein said second end is in communication with said first pressure sensing means, whereby pressure manually applied to said second pressure sensing means will cause said bellows means to move to a stop position defined by said stop means to produce said calibration output.

* * * * *